US012692220B2

(12) United States Patent
Xing et al.

(10) Patent No.: US 12,692,220 B2
(45) Date of Patent: Jul. 28, 2026

(54) POLYALKYL P-PHENYLENEDIAMINE ANTI-DEGRADANTS AND INTERMEDIATES AND PREPARATION METHOD THEREOF

(71) Applicant: Sennics Co., Ltd., Shanghai (CN)

(72) Inventors: Jinguo Xing, Shanghai (CN); Xiangyun Guo, Shanghai (CN); Gan Liang, Shanghai (CN); Jiaqiang Zhang, Shanghai (CN); Zhimin Tang, Shanghai (CN)

(73) Assignee: Sennics Co., Ltd., Shanghai (CN)

( * ) Notice: Subject to any disclaimer, the term of this patent is extended or adjusted under 35 U.S.C. 154(b) by 677 days.

(21) Appl. No.: 18/148,408

(22) Filed: Dec. 29, 2022

(65) Prior Publication Data

US 2024/0174592 A1 May 30, 2024

(30) Foreign Application Priority Data

Nov. 10, 2022 (CN) ........................ 202211406983.X

(51) Int. Cl.

| | |
|---|---|
| ***C07C 211/55*** | (2006.01) |
| ***B01J 21/18*** | (2006.01) |
| ***B01J 23/42*** | (2006.01) |
| ***B01J 25/02*** | (2006.01) |
| ***B01J 31/02*** | (2006.01) |
| ***C07C 209/26*** | (2006.01) |
| ***C08K 5/18*** | (2006.01) |
| ***C08L 7/00*** | (2006.01) |
| *B60C 1/00* | (2006.01) |

(52) U.S. Cl.

CPC ............. *C07C 211/55* (2013.01); *B01J 21/18* (2013.01); *B01J 23/42* (2013.01); *B01J 25/02* (2013.01); *B01J 31/0239* (2013.01); *C07C 209/26* (2013.01); *C08K 5/18* (2013.01); *C08L 7/00* (2013.01); *B01J 2231/44* (2013.01); *B01J 2531/002* (2013.01); *B60C 1/0016* (2013.01); *B60C 1/0025* (2013.01); *B60C 2001/0066* (2013.01); *C07C 2601/14* (2017.05); *C08L 2201/08* (2013.01)

(58) Field of Classification Search

CPC . C07C 211/55; C07C 209/26; C07C 2601/14; C08L 7/00; C08L 2201/08; B01J 21/18; B01J 23/42; B01J 25/02; B01J 31/0239; B01J 2231/44; B01J 2531/002; B60C 1/0016; B60C 1/0025; B60C 2001/0066; C08K 5/18

USPC .......................................................... 524/255

See application file for complete search history.

(56) References Cited

U.S. PATENT DOCUMENTS

| | | | |
|---|---|---|---|
| 3,565,856 | A | 2/1971 | Davies et al. |
| 10,793,510 | B2 | 10/2020 | Guo et al. |
| 10,829,615 | B2 | 11/2020 | Gao et al. |
| 11,008,281 | B2 | 5/2021 | Gao et al. |
| 2005/0065376 | A1 | 3/2005 | Wang et al. |
| 2007/0135657 | A1 | 6/2007 | Hobbs et al. |
| 2007/0173668 | A1 | 7/2007 | Wang et al. |
| 2012/0157714 | A1 | 6/2012 | Kim et al. |
| 2015/0045584 | A1 | 2/2015 | Nandi et al. |
| 2021/0230099 | A1 | 7/2021 | Gao et al. |

FOREIGN PATENT DOCUMENTS

| | | | | |
|---|---|---|---|---|
| CN | 1506349 | A | | 6/2004 |
| CN | 101906048 | A | | 12/2010 |
| CN | 103819346 | A | | 5/2014 |
| CN | 108299676 | A | | 7/2018 |
| CN | 113072741 | A | | 7/2021 |
| GB | 770299 | A | * | 3/1957 |
| GB | 1589887 | | | 5/1981 |

OTHER PUBLICATIONS

STN Structure Search Report, Chinese Patent Search Report by the Chinese IP Office, issued on Sep. 7, 2022.
U.S. Appl. No. 18/384,801, Jinguo Xing et al, filed Oct. 27, 2023.
STN. "CAS RN: 2663665-72-1 et al.," Registry, pp. 1-16 (Jul. 28, 2021).
STN. "CAS RN: 2663665-65-2 et al.," Registry, pp. 1-37 (Jul. 28, 2021).
U.S. Appl. No. 18/147,693, Xiaoyin Zhou et al., filed Dec. 28, 2022.
U.S. Appl. No. 18/148,370, Jinguo Xing et al., filed Dec. 29, 2022.
Tang, Zhimin, et al., "Research on the Process of Producing Blue Salt VB with New Green and Environmentally Friendly Technology," Shandong Chemical Industry, vol. 41, No. 10, pp. 18-24 (2012).
Office Action from Japanese Patent Office for Japanese Patent Application No. JP 2025-526864, total 14 pages including complete English translation thereof, mailed on Apr. 14, 2026.

* cited by examiner

*Primary Examiner* — Kelechi C Egwim
(74) *Attorney, Agent, or Firm* — Mei & Mark LLP; Manni Li

(57) ABSTRACT

A polyalkyl p-phenylenediamine antidegradant having a structure represented by Formula I, its intermediates and a preparation method thereof are provided. The polyalkyl p-phenylenediamine antidegradant provides good thermal oxidative aging resistance and UV aging resistance.

(I)

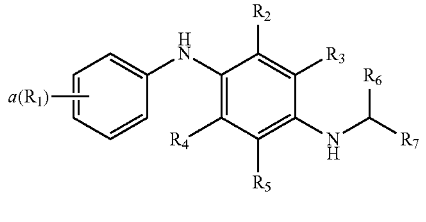

17 Claims, No Drawings

POLYALKYL P-PHENYLENEDIAMINE ANTI-DEGRADANTS AND INTERMEDIATES AND PREPARATION METHOD THEREOF

CROSS-REFERENCE TO RELATED APPLICATIONS

The subject application claims priority on Chinese Patent Application No. 202211406983. X filed on Nov. 10, 2022 in China. The contents and subject matters of the Chinese priority application are incorporated herein by reference.

TECHNICAL FIELD

The present invention belongs to the field of p-phenylenediamine antidegradants, specifically, a polyalkyl p-phenylenediamine antidegradant, its intermediates, and a preparation method thereof.

BACKGROUND

At present, p-phenylenediamine antidegradants, which are widely used in rubber products, especially tires, have efficient ozone protection performance, very good protection effect against flexural aging and general aging such as oxygen and heat, as well as a good protection effect against harmful metals such as copper and manganese. For example, the antidegradant 6PPD with the chemical name of N-(1,3-dimethylbutyl)-N'-phenyl-p-phenylenediamine, is a highly effective rubber antidegradant.

Chinese patent application publication CN113072741A discloses an environmentally friendly p-phenylenediamine antidegradant and a preparation method thereof. The structure of the environmentally friendly p-phenylenediamine antidegradant disclosed therein is as follows:

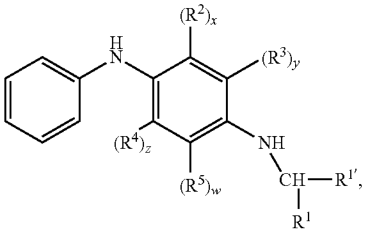

where the antidegradant will not be converted into quinone compounds after aging when the following specific conditions are met: at least one of x and w is 1, at least one of y and z is 1, and if x and z are 1 at the same time, y and w are not 0 at the same time. The preparation process provided by the patent application is as follows: firstly, aniline and p-bromonitrobenzene with the corresponding substituent group(s) undergo a C—N coupling reaction. The coupling product obtained from the reaction is subjected to a reduction reaction under catalytic conditions in a hydrogen atmosphere to obtain a reaction intermediate. The reaction intermediate and an aldehyde or a ketone undergo a reductive amination reaction under catalytic conditions to obtain the p-phenylenediamine antidegradant. In the process, the use of expensive bromide and precious metal organophosphorus complex catalysts are required, the conversion rate and yield of the reaction are not high, the separation and purification are complicated, and wastewater containing metal bromide salts is generated, which is not suitable for industrial production.

4-aminodiphenylamine is an important intermediate for making p-phenylenediamine antidegradants, which is generated by condensation and reduction of aniline or its derivatives and nitrobenzene under alkaline conditions. In addition, it can also be prepared by subjecting aniline and p-halogenated nitrobenzene to a C—N coupling reaction under the action of triphenylphosphorus-coordinated palladium as a catalyst to prepare anilino nitrobenzene, and then reducing the anilino nitrobenzene by hydrogenation.

Therefore, there is a need of a p-phenylenediamine antidegradant with novel structure and green preparation method for preparing the same.

SUMMARY OF THE INVENTION

To overcome the problems in the current technology, the present invention provides a p-phenylenediamine antidegradant with a novel structure, which has good thermal oxidative aging resistance and ultraviolet aging resistance. The present invention also provides a method for preparing the p-phenylenediamine antidegradant, which has the advantages of being green and environmentally friendly and no wastes discharged. The present invention also provides an intermediate for preparing the p-phenylenediamine antidegradant.

The present invention provides a compound of Formula I:

(I)

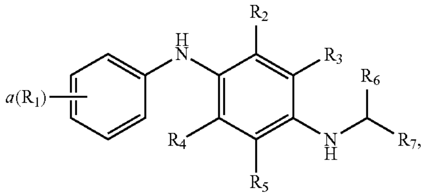

wherein each $R_1$ is independently selected and each is H, a C1-C18 chain hydrocarbon group, or a C3-C18 alicyclic hydrocarbon group; a is an integer in the range of 1 to 5; $R_2$, $R_3$, $R_4$, $R_5$ are each independently selected and each is H, a C1-C18 chain hydrocarbon group, or a C3-C18 alicyclic hydrocarbon group, and at least one of $R_2$, $R_3$, $R_4$, $R_5$ is not H; $R_6$, $R_7$ are each independently selected and each is a C1-C18 chain hydrocarbon group, a C3-C18 alicyclic hydrocarbon group, or $R_6$ forms a C3-C18 aliphatic ring with $R_7$.

In some embodiments of the compound of Formula I of the present invention, each $R_1$ is independently H or a C1-C8 alkyl.

In some embodiments of the present invention, a in formula I may be 1 or 2.

In some embodiments of the present invention, each of $R_2$, $R_3$, $R_4$, and $R_5$ is independently H or a C1-C8 alkyl.

In some embodiments of the present invention, two or three of $R_2$, $R_3$, $R_4$, $R_5$ are H.

In some embodiments of the present invention, $R_6$ and $R_7$ are each independently a C1-C8 alkyl or a C3-C8 cycloalkyl, or $R_6$ forms a C3-C8 aliphatic ring with $R_7$.

The present invention further provides a method for preparing the compound of Formula I, which comprises the following steps:

(1) reacting a compound of Formula A and a compound of Formula B in a condensation reaction in the presence of a first catalyst to obtain a condensate comprising a compound of Formula C, a compound of Formula C', or both, and then reducing the condensate under in the presence of $H_2$ and a second catalyst to obtain a compound of Formula II;

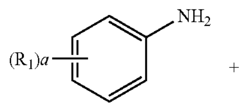

(A)

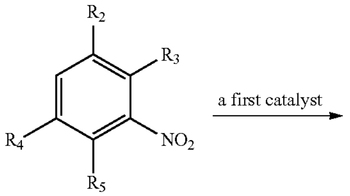

(B)

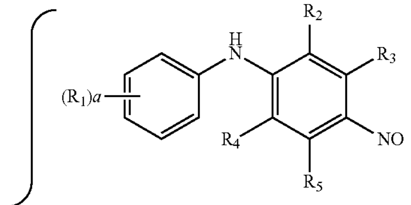

(C)

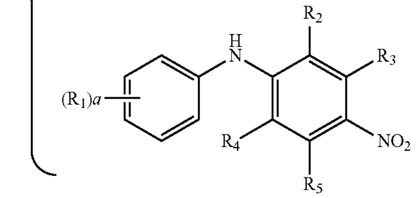

(C')

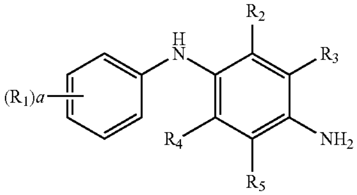

(II)

(2) reacting the compound of Formula II with a compound of Formula D in reductive alkylation reaction in the presence of $H_2$ and a third catalyst to obtain the compound of Formula I:

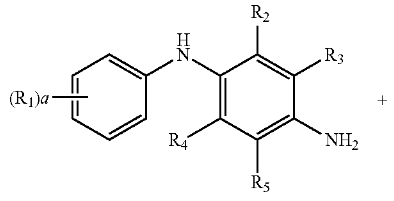

(II)

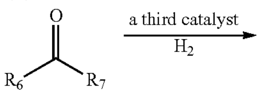

(D)

-continued

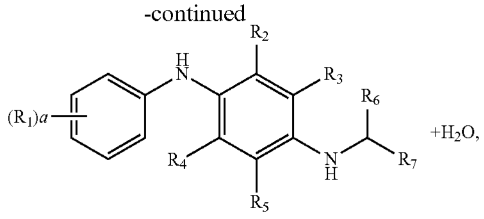

(I)

wherein $R_1$, $R_2$, $R_3$, $R_4$, $R_5$, $R_6$, and $R_7$ in the Formulae A, B, C, C', D, II, and I are as defined above in Formula I.

In the present invention, the first catalyst is an alkali metal hydroxide, an alkali metal alkoxide, a quaternary ammonium base, a combination of an alkali metal hydroxide and a halide of tetraalkyl ammonium, or a combination thereof.

In the present invention, the second catalyst is a porous metal catalyst or a supported metal catalyst. Preferably, the porous metal catalyst is Raney nickel, Raney cobalt, Raney copper, or a combination thereof; the metal in the supported metal catalyst is one or more of nickel, cobalt, copper, platinum, palladium, ruthenium, rhodium, or a combination thereof; and the support in the supported metal catalyst is carbon, alumina, silica gel, or molecular sieve.

In the present invention, the third catalyst is a supported metal catalyst. Preferably, the metal in the supported metal catalyst is one or more of nickel, cobalt, copper, platinum, palladium, ruthenium, or rhodium; and the support in the supported metal catalyst is one or more of carbon, alumina, silica gel, or molecular sieve.

In step (1) of the method of the present invention, the molar ratio of the compound of Formula A to the compound of Formula B is 2:1 to 15:1, and preferably 4:1 to 10:1.

In step (1) of the method of the present invention, the temperature of the condensation reaction is in a range of 40 to 90° C., and preferably 65 to 85° C.; and the vacuum degree is in a range of −0.09 to −0.99 MPa.

In the present invention, the temperature in the reaction of the condensate and $H_2$ is in a range of 40 to 120° C., and preferably 60 to 90° C.; and the hydrogen pressure is in a range of 0.5 to 5 MPa, and preferably 0.5 to 2.5 MPa.

In step (2) of the method of the present invention, the molar ratio of the compound of Formula D to the compound of Formula II is 1:1 to 15:1.

In step (2) of the method of the present invention, the reaction temperature is in a range of 40 to 150° C.; and the reaction pressure is in a range of 0.5 to 5 MPa.

The present invention also provides a compound of Formula II:

(II)

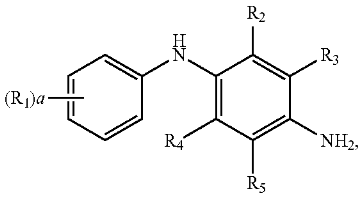

wherein $R_1$, $R_2$, $R_3$, $R_4$, $R_5$ and a are defined as above in Formula I.

In some embodiments of the compound of Formula II of the present invention, each $R_1$ is independently H or a C1-C8 alkyl.

In some embodiments of the compound of Formula II of the present invention, a is 1 or 2.

In some embodiments of the compound of Formula II of the present invention, $R_2$, $R_3$, $R_4$, and $R_5$ are each independently H or a C1-C18 alkyl.

In some embodiments of the compound of Formula II of the present invention, two to three of $R_2$, $R_3$, $R_4$, and $R_5$ are H.

The present invention further provides a method for preparing the compound of Formula II, which comprises the steps of reacting the compound of Formula A and the compound of Formula B in a condensation reaction in the presence of a first catalyst to obtain a condensate comprising the compound of Formula C, the compound of Formula C', or both, and then reducing the condensate in the presence of $H_2$ and a second catalyst to obtain a compound of Formula II;

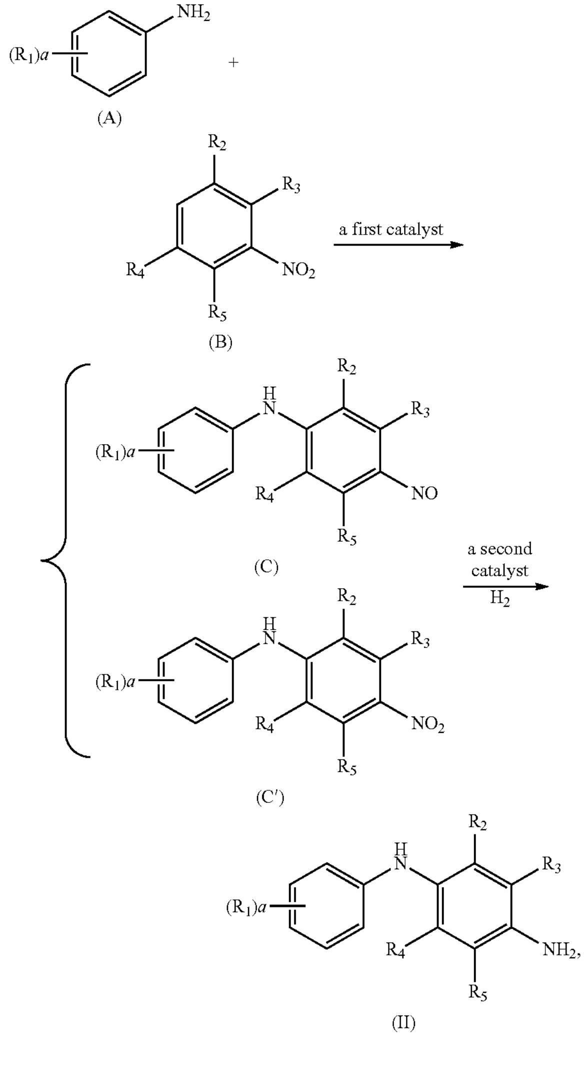

(A) (B) (C) (C') (II)

wherein $R_1$, $R_2$, $R_3$, $R_4$, and $R_5$ in Formulae A, B, C, C', and II are as defined above in Formula I.

In some embodiments of the method for preparing the compound of Formula II of the present invention, the first catalyst is one or more of an alkali metal hydroxide, an alkali metal alkoxide, a quaternary ammonium bases, or a combination of an alkali metal hydroxide and a halide of tetraalkyl ammonium.

In some embodiments of the method for preparing the compound of Formula II of the present invention, the second catalyst is a porous metal catalyst or a supported metal catalyst. Preferably, the porous metal catalyst is one or more of Raney nickel, Raney cobalt, or Raney copper; the metal in the supported metal catalyst is one or more of nickel, cobalt, copper, platinum, palladium, ruthenium, or rhodium; and the support in the supported metal catalyst is one or more of carbon, alumina, silica gel, or molecular sieve.

In step (1) of the method for preparing the compound of Formula II of the present invention, the molar ratio of the compound of Formula A to the compound of Formula B is 2:1 to 15:1, and preferably 4:1 to 10:1.

In step (1) of the method for preparing the compound of Formula II of the present invention, the temperature of the condensation reaction is in a range of 40 to 90° C., and preferably 65 to 85° C.; and the vacuum degree is in a range of −0.09 to −0.99 MPa.

In step (1) of the method for preparing the compound of Formula II of the present invention, the temperature of the reaction of the condensate and $H_2$ is in a range of 40 to 120° C., and preferably 60 to 90° C.; and the hydrogen pressure is in a range of 0.5 to 5 MPa, and preferably 0.5 to 2.5 MPa.

The present invention further provides a rubber composition, which comprises a compound of Formula I as described. The present invention further provides a rubber product comprising the rubber composition, and preferably, the rubber product is a tire.

The present invention also provides a method for improving thermal oxidative aging resistance and/or ultraviolet aging resistance of rubber or rubber products, comprising the step of adding a compound of Formula I of the present invention to rubber or rubber products.

DETAILED DESCRIPTION OF THE INVENTION

In the present invention, unless otherwise specified, percentage refers to mass percentage, and ratio refers to mass ratio.

In the present invention, when describing embodiments or examples, it should be understood that it is not intended to limit the present invention to these embodiments or examples. Conversely, all substitutes, modifications and equivalents of the methods and materials described in the present invention may be covered within the scope of the claims.

In the present invention, for the sake of conciseness, not all possible combinations of each technical feature in each embodiment or example are described. Thus, as long as there is no contradiction in the combination of these technical features, each technical feature in each embodiment or example may be arbitrarily combined, and all possible combinations should be considered to be within the scope of the specification.

In the present invention, a chain hydrocarbon group is a linear or branched saturated hydrocarbon group or unsaturated hydrocarbon group, usually containing 1 to 18 carbon atoms (a C1-C18 chain hydrocarbon group). Examples of a chain hydrocarbon group include, but are not limited to, methyl, ethyl, n-propyl, isopropyl, n-butyl, isobutyl, tert-butyl, n-hexyl, isohexyl, 1,3-dimethylbutyl, 1,4-dimethylpentyl, tert-octyl, vinyl, propenyl, and ethynyl.

In the present invention, an alicyclic hydrocarbon group is a group of carbon atoms bound in a cyclic form, usually containing 3 to 18 carbon atoms (a C3-C18 alicyclic hydrocarbon group). Examples of an alicyclic hydrocarbon group include, but are not limited to, isobornyl, cyclohexyl, norbornanyl, norbornenyl, dicyclopentadienyl, ethynyl cyclohexanyl, and ethynyl cyclohexenyl.

In the present invention, an alkyl group is a linear or branched monovalent saturated hydrocarbon group, usually containing 1 to 18 carbon atoms (C1-C18 alkyl), for examples, containing 1 to 8 carbon atoms (C1-C8 alkyl). Examples of an alkyl group include, but are not limited to, methyl, ethyl, propyl, 1-methylpropyl, isobutyl, and 1,3-dimethylbutyl.

In the present invention, a cycloalkyl group is a monovalent saturated hydrocarbon ring containing 3 to 18 carbon atoms, preferably containing 3 to 8 carbon atoms. Examples of a cycloalkyl group include, but are not limited to, cyclopropyl, cyclobutyl, cyclopentyl, cyclohexyl, cycloheptyl, cyclooctyl, and adamantyl.

Compound of Formula I

The polyalkyl-p-phenylenediamine compound having a structure represented by Formula I (referred to as a compound of Formula I) in the present invention can be used as a rubber antidegradant. Compared with the antidegradant 6PPD, it imparts better thermal oxidative aging resistance and ultraviolet aging resistance to rubber. The structure is as follows:

(I)

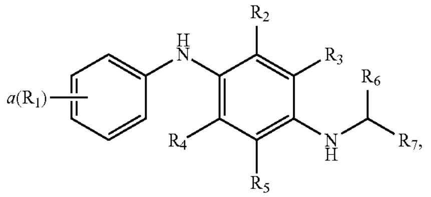

wherein each $R_1$ is independently H, a C1-C18 chain hydrocarbon group, or a C3-C18 alicyclic hydrocarbon group, and a is an integer of 1 to 5; $R_2$, $R_3$, $R_4$, and $R_5$ are each independently H, a C1-C18 chain hydrocarbon group, or a C3-C18 alicyclic hydrocarbon group, and at least one of $R_2$, $R_3$, $R_4$, and $R_5$ is not H; $R_6$ and $R_7$ are each independently a C1-C18 chain hydrocarbon group or a C3-C18 alicyclic hydrocarbon group, or $R_6$ forms a C3-C18 aliphatic ring with $R_7$.

Preferably, each $R_1$ is independently H or C1-C8 alkyl. In some embodiments, each $R_1$ is independently H, methyl, or ethyl. In some embodiments, each $R_1$ is independently H or methyl. In some embodiments, a is 1 or 2. When a is 1, $R_1$ is preferably at the ortho or para-position of the —NH-group. When a is 2, preferably, two $R_1$s are at the ortho and meta-positions of the —NH-group, respectively, and the two $R_1$s are adjacent to each other.

In some preferred embodiments, each $R_1$ is independently a C1-C8 alkyl. In some embodiments, each $R_1$ is independently a C1-C4 alkyl. In some embodiments, each $R_1$ is methyl. In some embodiments, a is 1 or 2. When a is 1, $R_1$ is preferably at the ortho or para-position of the —NH-group. When a is 2, preferably, two $R_1$s are at the ortho and meta-positions of the —NH-group, respectively, and the two $R_1$s are adjacent to each other.

Preferably, $R_2$, $R_3$, $R_4$, and $R_5$ are each independently H or a C1-C8 alkyl, and more preferably, two to three of $R_2$, $R_3$, $R_4$, and $R_5$ are H. In some embodiments, $R_2$, $R_3$, $R_4$, and $R_5$ are each independently H or a C1-C4 alkyl. In some embodiments, $R_2$, $R_3$, $R_4$, and $R_5$ are each independently H or methyl. When three of $R_2$, $R_3$, $R_4$, and $R_5$ are H, $R_2$ is preferably not H. When two of $R_2$, $R_3$, $R_4$, and $R_5$ are H, preferably, $R_2$ and $R_4$ are not H, or $R_2$ and $R_3$ are not H.

Preferably, $R_6$ and $R_7$ are each independently a C1-C8 alkyl or a C3-C8 cycloalkyl, or $R_6$ forms a C3-C8 aliphatic ring with $R_7$. In some embodiments, $R_6$ and $R_7$ are each independently a C1-C6 alkyl, for example, a C1-C4 alkyl, or $R_6$ forms a C5-C7 aliphatic ring, for example, a C6 aliphatic ring, with $R_7$. In some embodiments, $R_6$ is a C1-C2 alkyl, such as methyl, and $R_7$ is a C1-C6 alkyl, for example, a C1-C4 alkyl, or $R_6$ forms a C5-C7 aliphatic ring, for example, a C6 aliphatic ring, with $R_7$. Preferably, the aliphatic ring formed by $R_6$ and $R_7$ is a saturated aliphatic ring.

In some embodiments, each $R_1$ is independently H or a C1-C4 alkyl, or each $R_1$ is independently a C1-C4 alkyl; a is 1 or 2; $R_2$, $R_3$, $R_4$, and $R_5$ are each independently H or a C1-C4 alkyl, and preferably, two to three of $R_2$, $R_3$, $R_4$, and $R_5$ are H; $R_6$ and $R_7$ are each independently a C1-C6 alkyl, for example, a C1-C4 alkyl, or $R_6$ forms a C5-C7 aliphatic ring, for example, a C6 aliphatic ring, with $R_7$.

In some embodiments, each $R_1$ is independently H or a C1-C4 alkyl, preferably H or methyl, or each $R_1$ is independently a C1-C4 alkyl, for example, methyl; a is 1; $R_1$ is preferably at the ortho-position of the —NH-group; $R_2$, $R_3$, $R_4$, and $R_5$ are each independently H or a C1-C4 alkyl, preferably H and methyl, and more preferably, two to three of $R_2$, $R_3$, $R_4$, and $R_5$ are H and among which $R_2$ is not H, or $R_2$ and $R_3$ are not H; $R_6$, $R_7$ are each independently a C1-C6 alkyl, for example, a C1-C4 alkyl, or $R_6$ forms a C5-C7 aliphatic ring, for example, a C6 aliphatic ring, with $R_7$.

In some embodiments, the compound of Formula I is one of the following compounds:

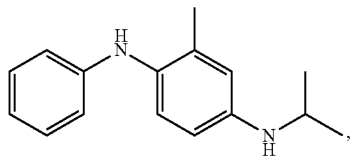

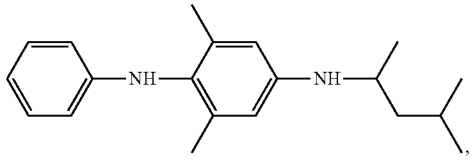

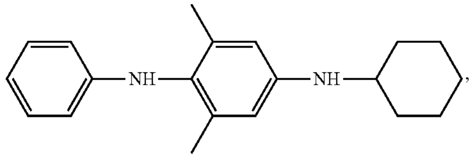

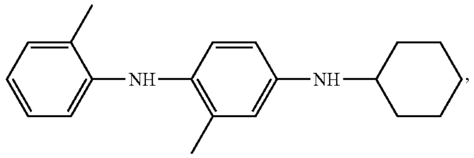

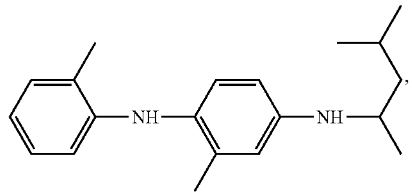

-continued

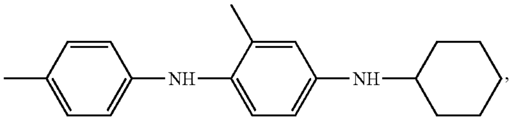

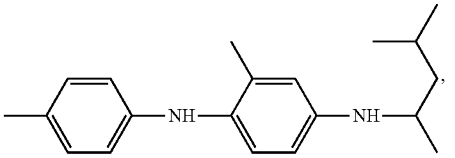

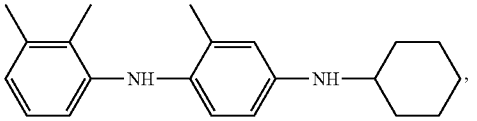

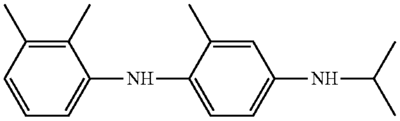

and

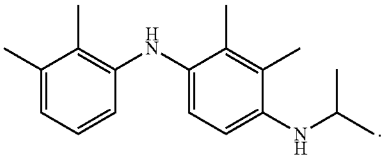 [SMILES: Cc1cccc(Nc2ccc(NC(C)C)c(C)c2C)c1C]

Compound of Formula II

The present invention also provides a compound of Formula II that may be used as an intermediate for preparing the compound of Formula I as follows:

(II)

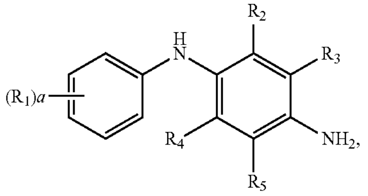

wherein $R_1$, a, $R_2$, $R_3$, $R_4$ and $R_5$ are as defined for the compound of Formula I.

In some embodiments, the compound of Formula II is one of the following compounds:

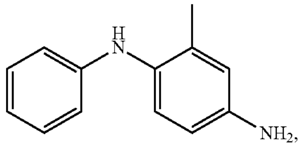

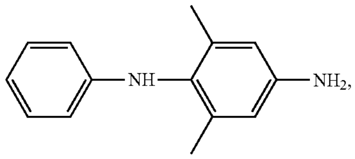

-continued

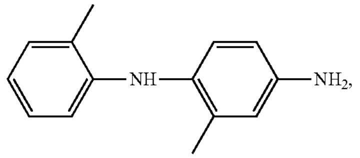

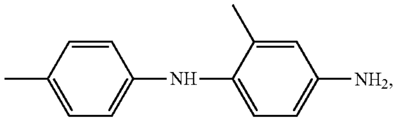

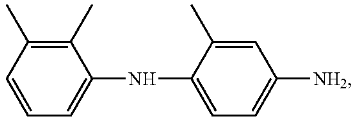

and

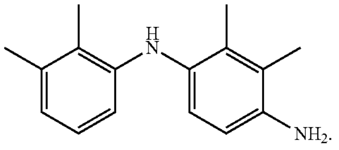

Method for Preparing Compound of Formula I and Compound of Formula II

The method for preparing the compound of Formula I and the compound of Formula II of the present invention comprises the following steps:

(1) reacting a compound of Formula A and a compound of Formula B in a condensation reaction in the presence of a first catalyst to obtain a condensate comprising a compound of Formula C, a compound of Formula C', or both, and reducing the condensate in the presence of $H_2$ and a second catalyst to obtain a compound of Formula II;

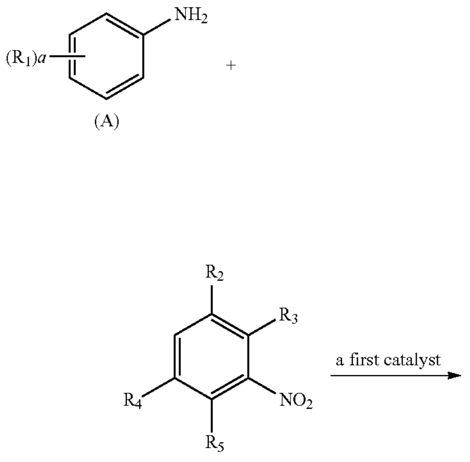

(A)

(B)

-continued

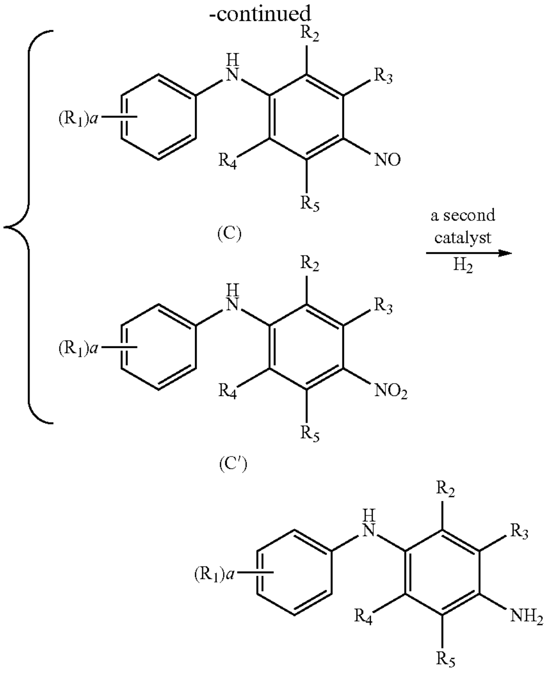

(C)

(C')

(II)

(2) reacting the compound of Formula II with a compound of Formula D in reductive alkylation in the presence of $H_2$ and a third catalyst to obtain the compound of Formula I;

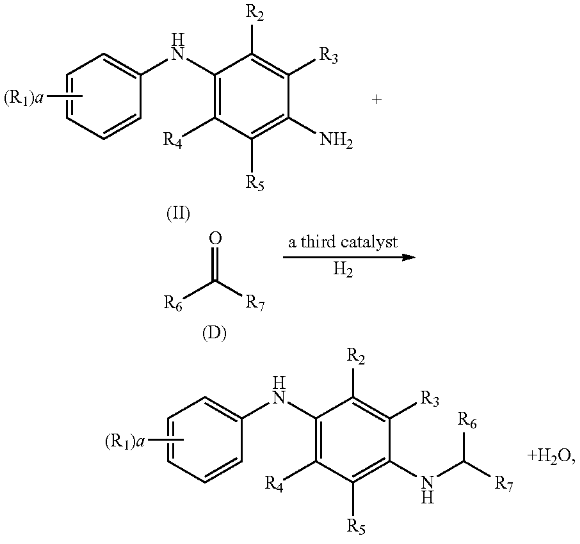

(II)

(D)

(I)

wherein $R_1$, $R_2$, $R_3$, $R_4$, $R_5$, $R_6$, and $R_7$ in Formulae A, B, C, C', D, II, and I are as defined in any of the embodiments herein.

The first catalyst used in step (1) may be one or more of an alkali metal hydroxide, an alkali metal alkoxide, a quaternary ammonium base, or a combination of an alkali metal hydroxide and a halide of tetraalkyl ammonium. Alkali metal hydroxides suitable for the present invention include sodium hydroxide, potassium hydroxide, and lithium hydroxide. Alkali metal alkoxides suitable for the present invention include sodium methoxide, potassium methoxide, sodium ethoxide, potassium ethoxide, sodium tert-butoxide, potassium tert-butoxide, sodium tert-pentoxide, and potassium tert-pentoxide. Quaternary ammonium bases are compounds having the general formula of $(R)_4NOH$, where R is four identical or different aliphatic hydrocarbon groups (such as alkyl) or aromatic groups. In some embodiments, each R group in the quaternary ammonium base is an alkyl, for example, each R may be independently methyl, ethyl, propyl, or butyl. Examples of quaternary ammonium bases suitable for the present invention include tetraalkylammonium hydroxides, for examples, tetramethylammonium hydroxide, tetraethylammonium hydroxide, and tetrabutylammonium hydroxide. The first catalyst may also be a combination of an alkali metal hydroxides and a halide of tetraalkyl ammonium. The halide of tetraalkyl ammonium has the general formula $(R)_4NX$, where R is four identical or different aliphatic hydrocarbon groups or aromatic groups, such as methyl, ethyl, propyl, butyl, etc., and X is a halogen atom, such as fluorine, chlorine, bromine, iodine. Examples of the combination of alkali metal hydroxides and halides of tetraalkyl ammonium include sodium hydroxide and tetrabutylammonium bromide. In some embodiments, the first catalyst is a quaternary ammonium base, such as tetraalkylammonium hydroxide. The molar ratio of the first catalyst to the compound of Formula A may be 0.1:1 to 2:1, preferably 0.1:1 to 0.5:1, such as 0.2:1, 0.3:1, and 0.4:1.

In some embodiments, in step (1), the compound of Formula A firstly reacts with the first catalyst to form a salt, and then the compound of Formula B is added dropwise for the condensation reaction.

In step (1), the condensate obtained by the condensation reaction of the compound of Formula A and the compound of Formula B in the presence of the first catalyst may be one or both of the nitro-compounds represented by Formula C and the nitroso-compounds represented by Formula C', and may also contain azobenzene compounds. The molar ratio of the compound of Formula A to the compound of Formula B may be 2:1 to 15:1, preferably 4:1 to 10:1, and more preferably 5:1 to 8:1, such as 6:1 or 7:1.

In step (1), the condensation reaction may be carried out in a range of 40 to 90° C., preferably 65 to 85° C., for examples, the reaction temperature may be at 60° C., 70° C., 75° C., or 80° C. The condensation reaction needs to be carried out under vacuum with a pressure in the range of −0.09 to −0.99 MPa.

The second catalyst in step (1) may be a porous metal catalyst or a supported metal catalyst. Porous metal catalysts are also known as sponge metal catalysts. Porous metal catalysts suitable for the present invention include Raney nickel (also known as skeleton nickel), Raney cobalt, and Raney copper. Supported metal catalysts include metals that act as centers of catalytic activity and supports that are used for supporting metals. The metal in the supported metal catalyst suitable for the present invention may be nickel, cobalt, copper, platinum, palladium, ruthenium, or rhodium. The support may be carbon, alumina, silica gel, or molecular sieve. The carbon as a support may be activated carbon. In some embodiments, the second catalyst is a porous metal catalyst, such as Raney nickel. The molar ratio of the metal in the second catalyst to the condensate may be 0.0001:1 to 0.2:1.

In step (1), the condensate generated by the condensation reaction is subjected to a hydrogenation reduction in the presence of a second catalyst to generate the compound of Formula II. In step (1), the reduction reaction may be carried out at 40 to 120° C., preferably 60 to 90° C., for examples, the reaction temperature may be 70° C., 75° C., and 80° C. The hydrogen pressure in the reduction reaction may be 0.5 to 5 MPa, preferably 0.5 to 2.5 MPa, such as 1 MPa, 1.5 MPa, 2 MPa, and 2.5 MPa.

In step (1), Compound C may also be used as a solvent, alternatively, solvents such as toluene or xylene may be used. At the end of the reaction in step (1), after the reaction solution is filtered to recover the second catalyst and the oil-water phase is separated to recover the first catalyst, the organic phase is distilled to remove the light components to obtain the compound of Formula II.

The third catalyst used in step (2) may be the aforementioned supported metal catalyst, such as Pt/C. The molar ratio of the metal in the third catalyst to the compound of Formula II may be 0.0001:1 to 0.2:1.

In step (2), the compound of Formula II and the compound of Formula D undergo hydro-reductive alkylation reaction in the presence of a third catalyst to generate the compound of Formula I. After the reaction, the carbon atom of carbonyl in the compound of Formula D is linked to the nitrogen atom of amino in the compound of Formula II. Therefore, the appropriate compound of Formula D can be selected for the reaction according to the $R_6$, $R_7$ groups in the compound of Formula II to be prepared. The molar ratio of the compound of Formula D to the compound of Formula II may be 1:1 to 15:1, such as 2:1, 3:1, 5:1, 8:1, 10:1, and 14:1. The reaction temperature of step (2) may be in a range of 40 to 150° C., preferably 50 to 120° C., such as 50° C., 70° C., 80° C., 100° C., and 120° C. The hydrogen pressure in step (2) may be 0.5 to 5 MPa, preferably 0.5 to 2.5 MPa, such as 1 MPa, 1.5 MPa, 2 MPa, and 2.5 MPa.

In step (2), the compound of Formula D as the starting material for reaction may also be used as the solvent. At the end of the reaction in step (2), the reaction liquid is filtered to recover the third catalyst and distilled under reduced pressure to remove the light components to obtain the compound of Formula II.

In the present invention, liquid chromatography (LC) or gas chromatography (GC) may be used to determine whether each step of the reaction reaches the endpoint, thereby determining the appropriate reaction time.

The method for preparing the compound of Formula I and the compound of Formula II according to the present invention is green and environmentally friendly, with substantially no wastewater during the preparation of the intermediate compound of Formula II. There is no need to use expensive bromide, and the catalysts can be recycled and reused.

Rubber Compositions and Rubber Products

The present invention also provides a rubber composition, which comprises the compound of Formula I if the present invention as an antidegradant. Hereinafter the compound of Formula I is referred to as the antidegradant of the present invention.

The raw materials of the rubber composition typically comprise diene elastomers, reinforcing fillers, antidegradants, and cross-linking agents. In the present invention, the rubber composition comprises unvulcanized rubber and vulcanized rubber. Vulcanized rubber may be prepared by vulcanizing (curing) unvulcanized rubber.

The raw materials of the rubber composition of the present invention comprises 100 parts by weight of a diene elastomer, 30 to 70 parts by weight of a reinforcing filler, 0.1 to 8 parts by weight of an antidegradant, and 0.5 to 3 parts by weight of a crosslinking agent. In the present invention, unless otherwise specified, the part by weight is based on 100 parts by weight of the diene elastomer contained in the raw material of the rubber composition.

In the present invention, diene elastomers refer to elastomers whose monomers comprise diolefins (such as butadiene, isoprene). Diene elastomers suitable for the present invention may be various diene elastomers known in the art, including, but not limited to, one or more of natural rubber (NR), cis-butadiene rubber (BR), isoprene rubber, styrene-butadiene rubber (SBR), chloroprene rubber (CR), nitrile rubber (NBR), isoprene/butadiene copolymer, isoprene/styrene copolymer, and isoprene/butadiene/styrene copolymer. In some embodiments, in the raw material of the rubber composition of the present invention, the diene elastomer comprises natural rubber and cis-butadiene rubber, or consists of natural rubber and cis-butadiene rubber. The mass ratio of natural rubber and cis-butadiene rubber may be 1:9 to 9:1, 2:8 to 8:2, 3:7 to 7:3, 4:6 to 6:4, 4.5:5.5 to 5.5:4.5, or 1:1. In some embodiments, the diene elastomer is natural rubber.

The raw materials of the rubber composition of the present invention typically comprise 0.1 to 8 parts by weight, preferably 1 to 5 parts by weight, and more preferably 2±0.5 parts by weight of the antidegradant. The rubber composition of the present invention is characterized in that the antidegradant therein is the antidegradant of the present invention. In the present invention, the antidegradant according to the present invention may account for not less than 50%, not less than 60%, not less than 80%, not less than 90% or 100% of the total mass of the antidegradant contained in the rubber composition.

The reinforcing filler suitable for the present invention may be a reinforcing filler conventionally used in a rubber composition, including, but not limited to, one or more selected from carbon black, titanium oxide, magnesium oxide, calcium carbonate, magnesium carbonate, aluminum hydroxide, magnesium hydroxide, clay, or talc. In some embodiments, in the rubber composition of the present invention, the reinforcing filler is carbon black. The raw material of the rubber composition typically comprises 30 to 70 parts by weight, preferably 40 to 60 parts by weight, and more preferably 45 to 55 parts by weight of the reinforced filler. In some embodiments, the raw material of the rubber composition of the present invention comprises 30 to 70 parts by weight, preferably 40 to 60 parts by weight, more preferably 45 to 55 parts by weight, such as 50±2 parts by weight of carbon black.

The crosslinking agent may be sulfur. The raw material of the rubber composition usually comprises 0.5 to 3 parts by weight, preferably 1 to 3 parts by weight of the crosslinking agent. In some embodiments, the raw material of the rubber composition of the present invention comprises 0.5 to 3 parts by weight, preferably 1 to 3 parts by weight, such as 2.5±0.5 parts by weight, 2.5±0.2 parts by weight of the crosslinking agent, such as sulfur.

The raw materials of the rubber composition of the present invention may also include other components commonly used in rubber compositions, including but not limited to one or more additives and accelerators. The respective amount of additives and accelerators may be a routine amount known in the art. The raw material of the rubber composition of the present invention may comprise 0 to 20 parts by weight, preferably 2 to 20 parts by weight of additives, and 0 to 1.5 parts by weight, preferably 0.2 to 1 part by weight of accelerators.

Additives may include softeners used to improve properties such as processability. Softeners may include petroleum-based softeners (operating oils) such as naphthenic oils, aromatic oils, processing oils, lubricating oils, paraffins, liquid paraffins, petroleum bitumen, and vaseline, and may also include fatty oil-based softeners such as stearic acid, castor oil, flaxseed oil, rapeseed oil, coconut oil, waxes (such as beeswax, carnauba wax and lanolin), tall oil, linoleic acid, palmitic acid, and lauric acid, etc. Additives may also include activating agents, such as zinc oxide, which can accelerate the vulcanization rate, improve thermal conductivity, wear resistance, and tear resistance of the rubber. Typically, a total of 2 to 20 parts by weight of additives is used per 100 parts by weight of diene elastomer. In some embodiments, the raw material of the rubber composition of the present invention comprises fatty oil-based softeners, such as stearic acid. The raw materials of the rubber composition of the present invention may comprise 0-5 parts by weight, preferably 0.5 to 4 parts by weight, more preferably 1 to 3 parts by weight, such as 2±0.5 parts by weight, 2±0.2 parts by weight of the fatty oil-based softener, such as stearic acid. In some embodiments, the raw material of the rubber composition of the present invention comprises an activating agent, such as zinc oxide. The raw material of the rubber composition of the present invention may comprise 0 to 10 parts by weight, preferably 2 to 8 parts by weight, more preferably 3 to 7 parts by weight, such as 5±1 parts by weight of the active agent, such as zinc oxide. In some embodiments, the raw materials of the rubber composition of the present invention include fatty oil-based softeners and activating agents. The respective amount of fatty oil-based softeners and activating agents may be as described above.

The accelerator is usually a vulcanization accelerator, which can be one or more of sulfonamide vulcanization accelerators, thiazole vulcanization accelerators, thiuram vulcanization accelerators, thiourea vulcanization accelerators, guanidine vulcanization accelerators, dithiocarbamate vulcanization accelerators, aldehyde amine vulcanization accelerators, aldehyde ammonia vulcanization accelerators, imidazoline vulcanization accelerators, or xanthonic acid vulcanization accelerators. For example, the accelerator may be the accelerator CBS (N-cyclohexyl-2-benzothiazole-sulfenamide). In some embodiments, the raw materials of the rubber composition of the present invention comprises an accelerator, such as the accelerator CBS. The raw material of the rubber composition of the present invention may comprise 0 to 1.5 parts by weight, preferably 0.2 to 1 part by weight, such as 0.6±0.2 parts by weight, 0.6±0.1 parts by weight of the accelerator, such as the accelerator CBS.

In addition, if it is required, the rubber compositions may further comprise plasticizers such as DMP (dimethyl phthalate), DEP (diethyl phthalate), DBP (dibutyl phthalate), DHP (diheptyl phthalate), DOP (dioctyl phthalate), DINP (diisononyl phthalate), DIDP (diisodecyl phthalate), BBP (butyl benzyl phthalate), DWP (dilauryl phthalate), and DCHP (dicyclohexyl phthalate). The amount of plasticizer may be a routine amount in the art. The raw material of the rubber composition of the present invention may comprise 0 to 10 parts by weight, preferably 0.1 to 5 parts by weight, more preferably 0.2 to 2 parts by weigh of the plasticizer.

The unvulcanized rubber of the present invention may be prepared by a conventional rubber mixing method, for example, it may be prepared by a two-stage mixing method, which comprises mixer mixing in a first stage comprising mixing diene elastomers, reinforcing fillers, additives, and antidegradants to obtain a master batch, and mill mixing in a second stage comprising mixing the master batch obtained in the first stage with a crosslinking agent and an accelerator to obtain an unvulcanized rubber.

The unvulcanized rubber of the present invention may be vulcanized by conventional vulcanization method to obtain a vulcanized rubber. The vulcanization temperature is usually 130° C. to 200° C., such as 140 to 160° C., 150±5° C. The vulcanization time depends on the vulcanization temperature, vulcanization system, and vulcanization kinetics, and is usually 10 to 60 minutes, such as 15±5 minutes or 15±2 minutes. Before vulcanization, conventional tableting can be performed on the kneaded unvulcanized rubber.

The present invention also provides a rubber product, which comprises the rubber composition according to any embodiment of the present invention. Rubber products may be tires, rubber shoes, sealing strips, sound insulation panels, or shock absorbing pads. In some embodiments, the rubber product is a tire, such as treads, belt layers, or sidewalls of a tire. The belt layer of the tire, in addition to the rubber composition of the present invention, may also comprise a reinforcing material conventionally used in the art.

The present invention also provides a method of using the compound of Formula I to improve the thermal oxidative aging resistance and/or ultraviolet aging resistance of rubber or rubber products. Preferably, the rubber product is a tire. The method of use comprises adding to rubber or rubber products the compound of Formula I of the present invention as an antidegradant.

The present invention is described in the following examples. These examples are merely illustrative and are not intended to limit the scope of the present invention. The methods, reagents, and materials used in the examples, unless otherwise stated, are conventional methods, reagents and materials in the art. The raw materials used in the examples are commercially available.

Example 1: Synthesis of Compound I-1(N-isopropyl-N'-phenyl-2-methyl-1,4-phenylenediamine)

(1) Synthesis of Compound II-1

139.7 g (1.5 mol) aniline and 91 g (0.25 mol) 25% aqueous solution of tetramethylammonium hydroxide (TMAOH) are added in a 500 mL four-mouth flask with stirring and the temperature is raised to 40 to 55° C. TMAOH and aniline are formed into salts by distillation and dehydration under reduced pressure. During the process, the color of the reaction liquid gradually changes from yellow to dark-red. The temperature is gradually raised to 72° C. When the amount of fraction is about 46 mL, 72° C. vacuum (−0.098 MPa) distillation and dropwise addition of 34.3 g (0.25 mol) 3-methyl nitrobenzene are performed at the same time with the dropwise addition time of about 3 hrs. After the dropwise addition, the temperature is kept for 1 hr. The reaction is monitored by LC chromatography until 3-methyl nitrobenzene is completely reacted. A condensate liquid is obtained.

The above condensate liquid is transferred to a 500 mL stainless steel reactor, to which 50 g deionized water and 40 g skeleton nickel catalyst are added. The atmosphere is replaced with hydrogen for three times, the temperature is raised to 75° C. and hydrogen is introduced to raise the pressure to be 1.5 MPa for hydro-reduction reaction. The reaction is monitored by LC until nitro-compounds and nitroso-compounds are completely reduced. The reaction liquid is filtered and separated to obtain an organic phase, and the organic phase is washed with water and distilled under reduced pressure (−0.1 MPa, 160° C.) to remove aniline and by-products of light components. Finally, the reduction product is rectified to obtain 42.6 g Compound II-1, which is cooled and solidified into a yellow solid. The yield is about 86% and its content is >99% by GC detection.

(II-1)

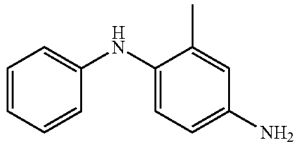

$^1$H NMR (400 MHz, $CDCl_3$) δ 7.22-7.15 (m, 2H), 7.03 (d, J=8.3 Hz, 1H), 6.79-6.74 (m, 1H), 6.68 (dt, J=8.8, 1.7 Hz, 2H), 6.61 (d, J=2.6 Hz, 1H), 6.54 (dd, J=8.3, 2.7 Hz, 1H), 5.15 (s, 1H), 3.56 (s, 2H), 2.17 (s, 3H).

(2) Synthesis of Compound I-1

40 g (0.2 mol) Compound II-1, 162.4 g (2.8 mol) acetone, and 0.5 g Pt/C are put into a reactor. The atmosphere is replaced with hydrogen for three times. The temperature is raised to 70° C., and hydrogen is introduced to raise the pressure to be 1.5 MPa for reaction. When the content of Compound II-1 is <0.1% by GC detection, the reaction is stopped. The temperature is cooled down. The catalyst is removed by filtration, and the light components are removed by distillation under reduced pressure of −0.1 MPa and at 180° C. to obtain 48.3 g Compound I-1 (yield at about 99.4%), and its content is >98% by GC detection. After cooled and solidified, it is a light pink solid.

(I-1)

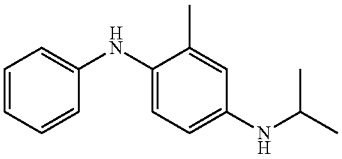

$^1$H NMR (400 MHz, $CDCl_3$) δ 7.20-7.11 (m, 2H), 7.03 (d, J=8.4 Hz, 1H), 6.77-6.70 (m, 1H), 6.65 (dt, J=8.8, 1.7 Hz, 2H), 6.50 (d, J=2.7 Hz, 1H), 6.44 (dd, J=8.4, 2.7 Hz, 1H), 5.13 (s, 1H), 3.71-3.43 (m, 1H), 3.34 (br s, 1H), 2.17 (s, 3H), 1.23 (d, J=6.3 Hz, 6H).

Example 2: Synthesis of Compound I-2(N-1,3-dimethylbutyl-N'-phenyl-2,6-dimethyl-1,4-phenylenediamine)

(1) Synthesis of Compound 11-2

186.2 g (2 mol) aniline and 91 g (0.25 mol) 25% aqueous solution of tetramethylammonium hydroxide (TMAOH) are added in a 500 mL four-mouth flask with stirring and the temperature is raised to 40 to 55° C. TMAOH and aniline are formed into salts by distillation and dehydration under reduced pressure. During the process, the color of the reaction liquid gradually changes from yellow to dark-red. The temperature is gradually raised to 72° C. When the amount of fraction is about 46 mL, 72° C. vacuum (−0.098 MPa) distillation and dropwise addition of 37.8 g (0.25 mol) 3,5-dimethyl nitrobenzene are performed at the same time with the dropwise addition time of about 3 hrs. After the dropwise addition, the temperature is kept for 1 hr. The reaction is monitored by LC chromatography until 3,5-dimethyl nitrobenzene is completely reacted. A condensate liquid is obtained.

The above condensate liquid is transferred to a 500 mL stainless steel reactor, to which 50 g deionized water and 50 g skeleton nickel catalyst are added. The atmosphere is replaced with hydrogen for three times, the temperature is raised to 75° C., and hydrogen is introduced to raise the pressure to be 1.5 MPa for hydro-reduction reaction. The reaction is monitored by LC until nitro-compounds and nitroso-compounds are completely reduced. The reaction liquid is filtered and separated to obtain an organic phase, and the organic phase is washed with water and distilled under reduced pressure (−0.1 MPa, 160° C.) to remove aniline and by-products of light components. Finally, the reduction product is rectified to obtain 44.3 g Compound 11-2, which is cooled and solidified into a light green solid. The yield is about 82% and its content is >98% by GC detection.

(II-2)

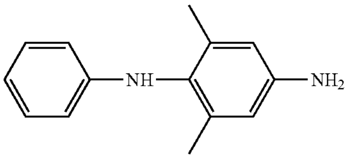

$^1$H NMR (400 MHz, $CDCl_3$) δ 7.15 (dd, J=17.7, 10.1 Hz, 2H), 6.70 (t, J=7.3 Hz, 1H), 6.49 (s, 2H), 6.47 (d, J=5.7 Hz, 2H), 4.98 (s, 1H), 3.55 (s, 2H), 2.14 (s, 6H).

$^{13}$C NMR (101 MHz, $CDCl_3$) δ 147.62, 144.52, 138.11, 129.47, 129.33, 117.47, 115.09, 112.85, 18.44.

(2) Synthesis of Compound 1-2

43.2 g (0.2 mol) Compound 11-2, 160.3 g (1.6 mol) 4-methyl-2-pentanone, and 0.5 g Pt/C are put into a reactor. The atmosphere is replaced with hydrogen for three times. The temperature is raised to 90° C., and hydrogen is introduced to raise the pressure to be 1.5 MPa for reaction. When the content of Compound 11-2 is <0.1% by GC detection, the reaction is stopped. The temperature is cooled down. The catalyst is removed by filtration, and the light components are removed by distillation under reduced pressure of −0.1 MPa and at 180° C. to obtain 59.5 g Compound 1-2 (yield at about 99.5%), and its content is >98.2% by GC detection. It is a dark red liquid at room temperature.

(I-2)

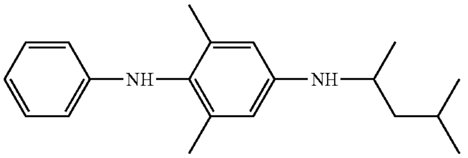

$^1$H NMR (400 MHz, $CDCl_3$) δ 7.13 (dd, J=8.4, 7.4 Hz, 2H), 6.68 (t, J=7.3 Hz, 1H), 6.48 (d, J=7.6 Hz, 2H), 6.36 (s, 2H), 4.97 (s, 1H), 3.62-3.39 (m, 1H), 3.28 (s, 1H), 2.14 (s, 6H), 1.87-1.71 (m, 1H), 1.45-1.52 (m, 1H), 1.35-1.23 (m, 1H), 1.18 (d, J=6.2 Hz, 3H), 0.97 (d, J=6.6 Hz, 3H), 0.95 (d, J=6.6 Hz, 3H).

$^{13}$C NMR (101 MHz, $CDCl_3$) δ 147.86, 145.96, 138.07, 129.25, 127.83, 117.21, 112.81, 112.73, 47.15, 46.71, 25.21, 23.07, 22.71, 21.28, 18.61.

Example 3: Synthesis of Compound 1-3 (N-cyclohexyl-N'-phenyl-2,6-dimethyl-1,4-phenylenediamine)

(1) Synthesis of Compound 11-2

The synthesis of Compound 11-2 is the same as Example 2.

(2) Synthesis of Compound 1-3

43.2 g (0.2 mol) Compound 11-2, 156.8 g (1.6 mol) cyclohexanone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-2 is <0.1% by GC detection, the reaction is stopped. The temperature is cooled down. The catalyst is removed by filtration, and the light components are removed by distillation at −0.1 MPa and 180° C. to obtain 59.6 g Compound 1-3 (yield at about 99.5%), and its content is >98.2% by GC detection. It is a dark red liquid at room temperature.

(I-3)

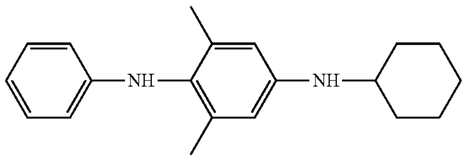

$^{1}H$ NMR (400 MHz, $CDCl_3$) δ 7.16 (dd, J=8.4, 7.4 Hz, 2H), 6.71 (t, J=7.3 Hz, 1H), 6.50 (d, J=7.6 Hz, 2H), 6.41 (s, 2H), 4.99 (s, 1H), 3.50 (s, 1H), 3.38-3.18 (m, 1H), 2.17 (s, 6H), 2.16-2.06 (m, 2H), 1.89-1.76 (m, 2H), 1.76-1.64 (m, 1H), 1.51-1.36 (m, 2H), 1.35-1.09 (m, 3H).

$^{13}C$ NMR (101 MHz, $CDCl_3$) δ 147.83, 145.62, 138.02, 129.21, 127.87, 117.18, 112.87, 112.69, 51.86, 33.69, 26.01, 25.11, 18.56.

Example 4: Synthesis of Compound 1-4 (N-cyclohexyl-N'-2-methylphenyl-2-methyl-1,4-phenylenediamine)

(1) Synthesis of Compound 11-4

160.5 g (1.5 mol) 2-methylaniline and 91 g (0.25 mol) 25% aqueous solution of tetramethylammonium hydroxide (TMAOH) are added in a 500 mL four-mouth flask with stirring and the temperature is raised to 40 to 50° C. TMAOH and 2-methylaniline are formed into salts by distillation and dehydration under reduced pressure. During the process, the color of the reaction liquid gradually changes from yellow to dark-red. The temperature is gradually raised to 72° C. When the amount of fraction is about 50% of the feeding amount of 25% tetramethylammonium hydroxide solution as a catalyst, 72° C. vacuum (−0.098 MPa) distillation and dropwise addition of 34.3 g (0.25 mol) 3-methyl nitrobenzene are performed at the same time with the dropwise addition time of about 3 hrs. After the dropwise addition, the temperature is kept for 1 hr. The reaction is monitored by LC chromatography until 3-methyl nitrobenzene is completely reacted. A condensate liquid is obtained.

The above condensate liquid is transferred to a 500 mL stainless steel reactor, to which 50 g deionized water and 40 g skeleton nickel catalyst are added. The atmosphere is replaced with hydrogen for three times, the temperature is raised to 75° C., and hydrogen is introduced to raise the pressure to be 1.5 MPa for reaction. The reaction is monitored by LC until nitro-compounds and nitroso-compounds are completely reduced. The reaction liquid is filtered, washed with water, and separated to obtain an organic phase, and the organic phase is distilled under reduced pressure (−0.1 MPa, 170° C.) to remove light components to obtain 42.8 g Compound 11-4. The yield is about 80% and its content is >98% by GC detection. It is a light-yellow solid at room temperature.

(II-4)

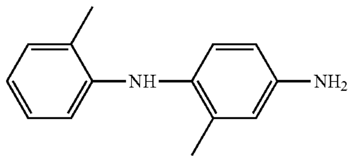

$^{1}H$ NMR (400 MHz, $CDCl_3$) δ 7.09 (d, J=7.3 Hz, 1H), 6.99 (t, J=7.7 Hz, 1H), 6.91 (d, J=8.2 Hz, 1H), 6.69 (t, J=7.3 Hz, 1H), 6.55 (s, 1H), 6.49 (dd, J=14.3, 5.2 Hz, 2H), 4.91 (s, 1H), 3.48 (br s, 2H), 2.23 (s, 3H), 2.11 (s, 3H).

$^{13}C$ NMR (101 MHz, $CDCl_3$) δ 144.96, 143.28, 134.47, 131.88, 130.36, 126.83, 126.36, 123.02, 118.25, 117.60, 113.65, 113.07, 17.90, 17.62.

(2) Synthesis of Compound 1-4

42.8 g (0.2 mol, purity at 99%) Compound 11-4, 156.8 g (1.6 mol) cyclohexanone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-4 is <0.1% by GC detection, the reaction is stopped. The temperature is cooled down. The catalyst is removed by filtration, and the light components are removed by distillation at −0.1 MPa and 180° C. to obtain 59.6 g Compound 1-4 (yield at about 99.5%), and its content is >98.2% by GC detection. It is a dark brown liquid at room temperature.

(I-4)

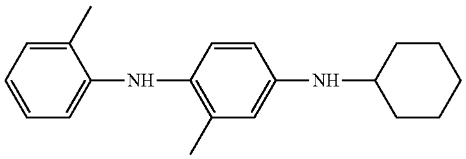

$^{1}H$ NMR (400 MHz, $CDCl_3$) δ 7.17 (d, J=7.3 Hz, 1H), 7.10-7.04 (m, 1H), 7.02 (d, J=8.4 Hz, 1H), 6.76 (td, J=7.3, 0.9 Hz, 1H), 6.60-6.56 (m, 2H), 6.51 (dd, J=8.4, 2.7 Hz, 1H), 4.99 (s, 1H), 3.51 (s, 1H), 3.37-3.23 (m, 1H), 2.33 (s, 3H), 2.21 (s, 3H), 2.18-2.10 (m, 2H), 1.90-1.80 (m, 2H), 1.78-1.69 (m, 1H), 1.52-1.39 (m, 2H), 1.37-1.16 (m, 3H).

$^{13}C$ NMR (101 MHz, $CDCl_3$) δ 145.36, 144.83, 134.97, 130.30, 130.26, 127.05, 126.85, 122.56, 117.88, 115.60, 112.70, 111.64, 52.10, 33.64, 26.00, 25.10, 18.12, 17.63.

Example 5: Synthesis of Compound I-5 (N-1,3-dimethylbutyl-N'-2-methylphenyl-2-methyl-1,4-phenylenediamine)

(1) Synthesis of Compound 11-4

The synthesis of Compound 11-4 is the same as Example 4.

(2) Synthesis of Compound I-5

43.2 g (0.2 mol, purity: 98%) Compound 11-4, 160.3 g (1.6 mol) 4-methyl-2-pentanone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-4 is <0.1% by GC detection, the reaction is stopped. The temperature is cooled down. The catalyst is removed by filtration, and the light components are removed by distillation at −0.1 MPa and 180° C. to obtain 59.6 g Compound I-5 (yield at about 99.5%), and its content is >98.2% by GC detection. It is a dark red liquid at room temperature.

(I-5)

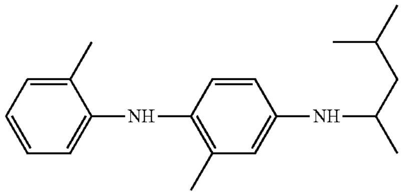

$^1$H NMR (400 MHz, $CDCl_3$) δ 7.15 (d, J=7.3 Hz, 1H), 7.08-7.03 (m, 1H), 7.01 (d, J=8.4 Hz, 1H), 6.74 (td, J=7.3, 1.0 Hz, 1H), 6.59-6.53 (m, 2H), 6.49 (dd, J=8.4, 2.7 Hz, 1H), 4.97 (s, 1H), 3.65-3.51 (m, 1H), 3.21 (br s, 1H), 2.31 (s, 3H), 2.19 (s, 3H), 1.90-1.75 (m, 1H), 1.59-1.47 (m, 1H), 1.38-1.28 (m, 1H), 1.22 (d, J=6.2 Hz, 3H), 1.01 (d, J=6.6 Hz, 3H), 0.99 (d, J=6.6 Hz, 3H).

$^{13}$C NMR (101 MHz, $CDCl_3$) δ 145.40, 145.20, 135.03, 130.35, 130.23, 127.11, 126.90, 122.60, 117.92, 115.55, 112.76, 111.53, 47.09, 46.93, 25.19, 23.08, 22.68, 21.23, 18.18, 17.67.

Example 6: Synthesis of Compound 1-6 (N-cyclohexyl-N'-4-methylphenyl-2-methyl-1,4-phenylenediamine)

(1) Synthesis of Compound 11-6

160.5 g (1.5 mol) 4-methylaniline and 100.1 g (0.275 mol) 25% aqueous solution of tetramethylammonium hydroxide (TMAOH) are added in a 500 mL four-mouth flask with stirring and the temperature is raised to 40 to 50° C. TMAOH and 4-methylaniline are formed into salts by distillation and dehydration under reduced pressure. During the process, the color of the reaction liquid gradually changes from yellow to dark-red. The temperature is gradually raised to 72° C. When the amount of fraction is about 50% of the feeding amount of 25% tetramethylammonium hydroxide solution as a catalyst, 72° C. vacuum (−0.098 MPa) distillation and dropwise addition of 34.3 g (0.25 mol) 3-methyl nitrobenzene are performed at the same time with the dropwise addition time of about 3 hrs. After the dropwise addition, the temperature is kept for 1 hr. The reaction is monitored by LC chromatography until 3-methyl nitrobenzene is completely reacted. A condensate liquid is obtained.

The above condensate liquid is transferred to a 500 mL stainless steel reactor, to which 50 g deionized water and 40 g skeleton nickel catalyst are added. The atmosphere is replaced with hydrogen for three times, the temperature is raised to 75° C., and hydrogen is introduced to raise the pressure to be 1.5 MPa for reaction. The reaction is monitored by LC until nitro-compounds and nitroso-compounds are completely reduced. The reaction liquid is filtered, washed with water, and separated to obtain an organic phase, and the organic phase is distilled under reduced pressure (−0.1 MPa, 170° C.) to remove light components to obtain 46.1 g Compound 11-6. The yield is about 86% and its content is >98% by GC detection. It is a light-yellow solid at room temperature.

(II-6)

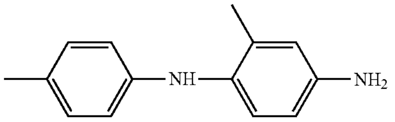

$^1$H NMR (400 MHz, $CDCl_3$) δ 7.01 (t, J=6.6 Hz, 3H), 6.67-6.63 (m, 2H), 6.62 (d, J=2.5 Hz, 1H), 6.55 (dd, J=8.3, 2.6 Hz, 1H), 5.02 (s, 1H), 3.38 (s, 2H), 2.29 (s, 3H), 2.19 (s, 3H).

$^{13}$C NMR (101 MHz, $CDCl_3$) δ 144.36, 142.87, 133.94, 132.41, 129.72, 127.73, 125.32, 117.69, 114.90, 113.67, 20.47, 17.99.

(2) Synthesis of Compound 1-6

42.8 g (0.2 mol, purity: 99%) Compound 11-6, 156.8 g (1.6 mol) cyclohexanone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-6 is <0.1% by GC detection, the reaction is stopped. The temperature is cooled down. The catalyst is removed by filtration, and the light components are removed by distillation at −0.1 MPa and 180° C. to obtain 59.6 g Compound 1-6 (yield at about 99.5%), and its content is >98.2% by GC detection. It is a dark brown liquid at room temperature.

(I-6)

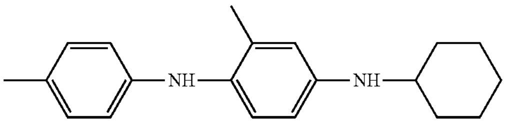

$^1$H NMR (400 MHz, $CDCl_3$) δ 6.99 (t, J=8.2 Hz, 3H), 6.60 (d, J=8.4 Hz, 2H), 6.51 (d, J=2.5 Hz, 1H), 6.45 (dd, J=8.4, 2.7 Hz, 1H), 5.04 (s, 1H), 3.40 (s, 1H), 3.29-3.17 (m, 1H), 2.26 (s, 3H), 2.17 (s, 3H), 2.12-2.04 (m, 2H), 1.83-1.75 (m, 2H), 1.72-1.61 (m, 1H), 1.51-1.31 (m, 2H), 1.28-1.13 (m, 3H).

$^{13}$C NMR (101 MHz, $CDCl_3$) δ 144.85, 144.56, 134.52, 130.81, 129.71, 127.39, 126.12, 115.71, 114.54, 111.69, 52.22, 33.70, 26.03, 25.12, 20.48, 18.22.

Example 7: Synthesis of Compound 1-7 (N-1,3-dimethylbutyl-N'-4-methylphenyl-2-methyl-1,4-phenylenediamine)

(1) Synthesis of Compound 11-6

The synthesis of Compound 11-6 is the same as Example 6

(2) Synthesis of Compound 1-7

43.2 g (0.2 mol, purity: 98%) Compound 11-6, 160.3 g (1.6 mol) 4-methyl-2-pentaone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-6 is <0.1% by GC detection, the reaction is stopped. The temperature is cooled down. The catalyst is removed by filtration, and the light components are removed by distillation at −0.1 MPa and 180° C. to obtain 59.6 g Compound 1-7 (yield at about 99.5%), and its content is >98.2% by GC detection. It is a dark red liquid at room temperature.

(I-7)

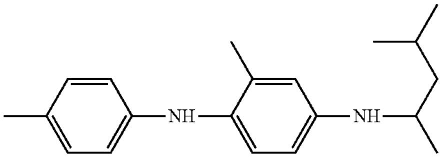

$^1$H NMR (400 MHz, $CDCl_3$) δ 6.96 (dd, J=9.8, 8.6 Hz, 3H), 6.57 (d, J=8.4 Hz, 2H), 6.46 (d, J=2.3 Hz, 1H), 6.40 (dd, J=8.4, 2.5 Hz, 1H), 4.98 (s, 1H), 3.58-3.40 (m, 1H), 3.25 (br s, 1H), 2.22 (s, 3H), 2.14 (s, 3H), 1.82-1.68 (m, 1H), 1.52-1.36 (m, 1H), 1.31-1.19 (m, 1H), 1.15 (d, J=6.2 Hz, 3H), 0.94 (d, J=6.6 Hz, 3H), 0.92 (d, J=6.6 Hz, 3H).

$^{13}$C NMR (101 MHz, $CDCl_3$) δ 144.92, 134.61, 130.72, 129.74, 127.34, 126.24, 115.60, 114.55, 111.51, 47.13, 46.99, 25.21, 23.10, 22.71, 21.26, 20.52, 18.27.

Example 8: Synthesis of Compound 1-8 (N-cyclohexyl-N'-2,3-dimethylphenyl-2-methyl-1,4-phenylenediamine)

(1) Synthesis of Compound 11-8

181.5 g (1.5 mol) 2,3-dimethylaniline and 100.1 g (0.275 mol) 25% aqueous solution of tetramethylammonium hydroxide (TMAOH) are added in a 500 mL four-mouth flask with stirring and the temperature is raised to 40 to 50° C. TMAOH and 2,3-dimethylaniline are formed into salts by distillation and dehydration under reduced pressure. During the process, the color of the reaction liquid gradually changes from yellow to dark-red. The temperature is gradually raised to 72° C. When the amount of fraction is about 50% of the feeding amount of 25% tetramethylammonium hydroxide solution as a catalyst, 72° C. vacuum (−0.098 MPa) distillation and dropwise addition of 34.3 g (0.25 mol) 3-methyl nitrobenzene are performed at the same time with the dropwise addition time of about 3 hrs. After the dropwise addition, the temperature is kept for 1 hr. The reaction is monitored by LC chromatography until 3-methyl nitrobenzene is completely reacted. A condensate liquid is obtained.

The above condensate liquid is transferred to a 500 mL stainless steel reactor, to which 50 g deionized water and 40 g skeleton nickel catalyst are added. The atmosphere is replaced with hydrogen for three times, the temperature is raised to 75° C., and hydrogen is introduced to raise the pressure to be 1.5 MPa for reaction. The reaction is monitored by LC until nitro-compounds and nitroso-compounds are completely reduced. The reaction liquid is filtered, washed with water, and separated to obtain an organic phase, and the organic phase is distilled under reduced pressure (−0.1 MPa, 180° C.) to remove light components to obtain 46.6 g Compound 11-8. The yield is about 80% and its content is >97% by GC detection. After cooled, it is a light-yellow solid.

(II-8)

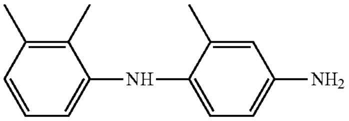

$^1$H NMR (400 MHz, $CDCl_3$) δ 6.93 (t, J=7.8 Hz, 1H), 6.88 (d, J=8.3 Hz, 1H), 6.68 (d, J=7.4 Hz, 1H), 6.62 (d, J=2.1 Hz, 1H), 6.58-6.50 (m, 1H), 6.46 (d, J=8.1 Hz, 1H), 4.95 (s, 1H), 3.53 (s, 2H), 2.33 (s, 3H), 2.19 (s, 3H), 2.16 (s, 3H).

$^{13}$C NMR (101 MHz, $CDCl_3$) δ 144.73, 142.86, 137.04, 133.81, 132.84, 125.97, 125.55, 122.39, 120.95, 117.73, 113.75, 112.33, 20.72, 17.98, 12.99.

(2) Synthesis of Compound 1-8

46.6 g (0.2 mol) Compound 11-8, 156.8 g (1.6 mol) cyclohexanone, and 0.5 g Pt/C catalyst are put into a reactor. The atmosphere is replaced with hydrogen for three times. The temperature is raised to 100° C., and hydrogen is introduced to raise the pressure to be 1.5 MPa for reaction. When the content of Compound 11-8 is <0.1% by GC detection, the reaction is stopped. The temperature is cooled down. The catalyst is removed by filtration, and the light components are removed by distillation at −0.1 MPa and 180° C. to obtain 65.9 g Compound 1-8 (yield at about 99.5%), and its content is >97.6% by GC detection. It is a red liquid at room temperature.

(I-8)

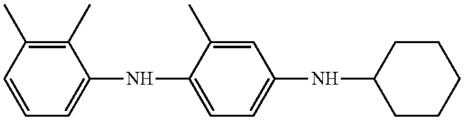

$^1$H NMR (400 MHz, $CDCl_3$) δ 7.02-6.86 (m, 2H), 6.68 (d, J=7.4 Hz, 1H), 6.54 (d, J=2.6 Hz, 1H), 6.51-6.41 (m, 2H), 4.96 (s, 1H), 3.51 (br s, 1H), 3.39-3.07 (m, 1H), 2.35 (s, 3H), 2.22 (s, 3H), 2.18 (s, 3H), 2.16-2.05 (m, 2H), 1.88-1.76 (m, 2H), 1.75-1.64 (m, 1H), 1.49-1.34 (m, 2H), 1.34-1.11 (m, 3H).

$^{13}$C NMR (101 MHz, $CDCl_3$) δ 145.18, 144.54, 136.88, 134.42, 131.08, 126.40, 125.95, 121.69, 120.48, 115.72, 111.74, 52.21, 33.70, 26.04, 25.13, 20.71, 18.16, 12.90.

Example 9: Synthesis of Compound I-9 (N-isopropyl-N'-2,3-dimethylphenyl-2-methyl-1,4-phenylenediamine)

(1) Synthesis of Compound 11-8

The synthesis of Compound 11-8 is the same as Example 8

(2) Synthesis of Compound 1-9

46.6 g (0.2 mol) Compound 11-8, 162.4 g (2.8 mol) acetone, and 0.5 g Pt/C catalyst are put into a reactor. The atmosphere is replaced with hydrogen for three times. The temperature is raised to 70° C., and hydrogen is introduced to raise the pressure to be 1.5 MPa for reaction. When the content of Compound 11-8 is <0.1% by GC detection, the reaction is stopped. The temperature is cooled down. The catalyst is removed by filtration, and the light components are removed by distillation at −0.1 MPa and 180° C. to obtain 54.9 g Compound 1-9 (yield at about 99.5%), and its content is >97% by GC detection. It is a gray-white solid at room temperature.

(I-9)

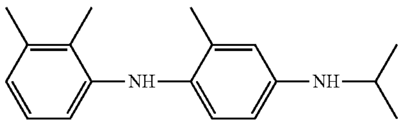

$^1$H NMR (400 MHz, $CDCl_3$) δ 7.01-6.93 (m, 2H), 6.71 (d, J=7.4 Hz, 1H), 6.57 (d, J=2.6 Hz, 1H), 6.50 (dd, J=8.3, 2.8 Hz, 2H), 4.99 (br s, 1H), 3.78-3.56 (m, 1H), 3.13 (br s, 1H), 2.38 (s, 3H), 2.24 (s, 3H), 2.21 (s, 3H), 1.28 (d, J=6.3 Hz, 6H).

$^{13}$C NMR (101 MHz, $CDCl_3$) δ 145.10, 144.59, 136.85, 134.30, 131.20, 126.28, 125.92, 121.71, 120.29, 115.81, 111.81, 111.78, 44.66, 23.15, 20.68, 18.13, 12.88.

Example 10: Synthesis of Compound I-10 (N-isopropyl-N'-2,3-dimethylphenyl-2,3-dimethyl-1,4-phenylenediamine)

(1) Synthesis of Compound II-10

181.5 g (1.5 mol) 2,3-dimethylaniline and 100.1 g (0.275 mol) 25% aqueous solution of tetramethylammonium hydroxide (TMAOH) are added in a 500 mL four-mouth flask with stirring and the temperature is raised to 40 to 50° C. TMAOH and 2,3-dimethylaniline are formed into salts by distillation and dehydration under reduced pressure. During the process, the color of the reaction liquid gradually changes from yellow to dark-red. The temperature is gradually raised to 72° C. When the amount of fraction is about 50% of the feeding amount of 25% tetramethylammonium hydroxide solution as a catalyst, 72° C. vacuum (−0.098 MPa) distillation and dropwise addition of 37.8 g (0.25 mol) 2,3-dimethyl nitrobenzene are performed at the same time with the dropwise addition time of about 3 hrs. After the dropwise addition, the temperature is kept for 2 hrs. The reaction is monitored by LC chromatography until 2,3-dimethyl nitrobenzene is completely reacted. A condensate liquid is obtained.

The above condensate liquid is transferred to a 500 mL stainless steel reactor, to which 50 g deionized water and 40 g skeleton nickel catalyst are added. The atmosphere is replaced with hydrogen for three times, the temperature is raised to 75° C., and hydrogen is introduced to raise the pressure to be 1.5 MPa for reaction. The reaction is monitored by LC until nitro-compounds and nitroso-compounds are completely reduced. The reaction liquid is filtered, washed with water, and separated to obtain an organic phase, and the organic phase is distilled under reduced pressure (−0.1 MPa, 180° C.) to remove light components to obtain 47.5 g Compound II-10. The yield is about 76% and its content is >96% by GC detection. After cooled, it is a light-yellow liquid.

(II-10)

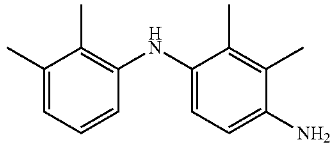

$^1$H NMR (400 MHz, $CDCl_3$) δ 6.91 (t, J=7.9 Hz, 1H), 6.87 (d, J=8.3 Hz, 1H), 6.67 (d, J=7.5 Hz, 1H), 6.58 (d, J=8.2 Hz, 1H), 6.27 (d, J=8.2 Hz, 1H), 4.93 (s, 1H), 3.52 (s, 2H), 2.35 (s, 3H), 2.21 (s, 3H), 2.18 (s, 3H), 2.16 (s, 3H).

(2) Synthesis of Compound I-10

37.5 g (0.15 mol) Compound II-10, 162.4 g (2.8 mol) acetone, and 0.5 g Pt/C catalyst are put into a reactor. The atmosphere is replaced with hydrogen three times. The temperature is raised to 70° C., and hydrogen is introduced to raise the pressure to be 1.5 MPa for reaction. When the content of Compound II-10 is <0.1% by GC detection, the reaction is stopped. The temperature is cooled down. The catalyst is removed by filtration, and the light components are removed by distillation at −0.1 MPa and 180° C. to obtain 43.7 g Compound I-10 (yield at about 99.4%), and its content is >96% by GC detection. It is a gray-white solid at room temperature.

(I-10)

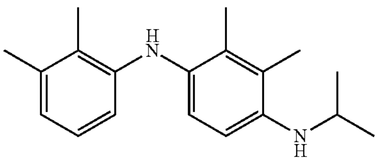

$^1$H NMR (400 MHz, $CDCl_3$) δ 6.90 (t, J=7.7 Hz, 1H), 6.84 (d, J=8.0 Hz, 1H), 6.57 (d, J=7.5 Hz, 1H), 6.55 (d, J=8.1 Hz, 1H), 6.23 (d, J=8.1 Hz, 1H), 4.95 (s, 1H), 3.76-3.53 (m, 1H), 3.12 (s, 1H), 2.35 (s, 3H), 2.21 (s, 3H), 2.17 (s, 6H), 1.29 (d, J=6.2 Hz, 6H).

Test Example

Rubber stocks 1-4 are prepared according to the formulation shown in Table 1 using the following steps.

1. Natural rubber SCRS is added to a mixer and kneaded for a period of time. Carbon black N330, aromatic oil, zinc oxide, stearic acid, and an antioxidant (6PPD, Compound I-1, Compound 1-2 or Compound 1-4) are added and continuously kneaded until they are evenly mixed. The temperature is controlled between 150° C. and 160° C. during kneading.
2. The whole mixture is cooled to below 100° C., and then a crosslinking system (sulfur S and an accelerator CBS) is added for kneading the whole mixture. The temperature during kneading is controlled to be not more than 110° C.
3. The obtained rubber composition is calendered into sheets (thickness of 2-3 mm), vulcanized at a vulcanization temperature of 150° C. for 15 minutes.

The sources of the materials in Table 1 are as follows:

SCRS: Xishuangbanna Sinochem Rubber Co., Ltd., Natural rubber SCRS;

N330: Cabot Corporation, Carbon Black N330;

Stearic acid: Shanghai Titan Scientific Co., Ltd. a general reagent stearic acid (AR);

Zinc oxide: Shanghai Titan Scientific Co., Ltd., a general reagent zinc oxide (AR);

CBS is the vulcanization accelerator CBS manufactured by Sennics Co., Ltd.;

S: Sinopharm Chemical Reagent Company, sublimed sulfur (AR);

6PPD is the antidegradant SIRANTOX 6PPD manufactured by Sennics Co., Ltd.; Compound I-1 is the compound synthesized in Example 1; Compound 1-2: the compound synthesized in Example 2; Compound 1-4: the compound synthesized in Example 4.

TABLE 1

| Rubber stock formulation (unit: part by mass) | | | | |
|---|---|---|---|---|
| Formulation | Rubber Stock 1 | Rubber Stock 2 | Rubber Stock 3 | Rubber Stock 4 |
| SCR5 | 100.0 | 100.0 | 100.0 | 100.0 |
| N330 | 50.0 | 50.0 | 50.0 | 50.0 |
| Zinc oxide | 5.0 | 5.0 | 5.0 | 5.0 |
| Stearic acid | 2.0 | 2.0 | 2.0 | 2.0 |
| 6PPD | 2.5 | | | |
| Compound I-1 | | 2.5 | | |
| Compound I-2 | | | 2.5 | |
| Compound I-4 | | | | 2.5 |
| CBS | 0.6 | 0.6 | 0.6 | 0.6 |
| S | 2.5 | 2.5 | 2.5 | 2.5 |
| Total | 162.6 | 162.6 | 162.6 | 162.6 |

The anti-ultraviolet aging test of the rubber stocks 1-4 is performed according to GB/T 16585 rubber, vulcanized-test method of resistance to artificial weathering (Fluorescent UV lamp). The test conditions, parameters, and steps are shown in Table 2, and the test results are shown in Table 3.

The physical properties (tensile strength, elongation at break) of the rubber stocks 1-4 are determined according to GB/T 528-2009 rubber, vulcanized or thermoplastic-determination of tensile stress-strain properties, and the results are shown in Table 3.

The thermal oxidative aging test of the rubber stocks 1-4 is performed according to GB/T 3512-2014 rubber, vulcanized or thermoplastic-accelerated aging and heat resistance test. Test conditions: 100° C.*48 hours, and the test results are shown in Table 3.

TABLE 2

| UV aging resistance test parameters and test procedures Lamp Model: UVA-340 Total aging time: 168 hours | | | | |
|---|---|---|---|---|
| Test step | Function | UV light intensity($W/m^2$) | Temperature (° C.) | Time (hour) |
| 1 | ultraviolet | 0.89 | 60 | 8 |
| 2 | condensation | N/A | 50 | 4 |
| 3 | Turn to step 1 | | | |

TABLE 3

| Original and After-aging physical properties of vulcanized rubber | | | | | |
|---|---|---|---|---|---|
| | Test item | Rubber Stock 1 | Rubber Stock 2 | Rubber Stock 3 | Rubber Stock 4 |
| Original physical properties | Tensile strength/MPa | 25.5 | 25.4 | 25.3 | 25.7 |
| | Elongation at break/% | 485 | 480 | 483 | 472 |
| | Tensile product | 12367 | 12192 | 12220 | 12130 |
| Physical properties after thermal oxidative aging | Tensile strength/MPa | 21.1 | 22.0 | 22.1 | 21.8 |
| | Elongation at break/% | 331 | 365 | 375 | 355 |
| | Tensile product | 6984 | 8030 | 8288 | 7739 |
| | Physical property retention/% | 56.4 | 65.8 | 67.8 | 63.8 |
| physical properties | Tensile strength/MPa | 24.3 | 24.6 | 24.9 | 24.7 |
| | Elongation at break/% | 435 | 452 | 456 | 450 |

TABLE 3-continued

| Original and After-aging physical properties of vulcanized rubber | | | | | |
|---|---|---|---|---|---|
| | Test item | Rubber Stock 1 | Rubber Stock 2 | Rubber Stock 3 | Rubber Stock 4 |
| after UV aging | Tensile product | 10571 | 11119 | 11354 | 11115 |
| | Physical property retention/% | 85.5 | 91.2 | 92.9 | 91.6 |

The test results in Table 3 show that the thermal oxidative aging resistance and UV aging resistance of the rubber stocks 2-4 containing the antidegradants of the present invention are better than the rubber stock 1 containing 6PPD. In terms of thermal oxidative aging resistance after aging at 100° C.*48 hours, the physical property retention rate of the rubber stocks 2-4 is increased by about 10% compared with the rubber stock 1. In terms of UV aging resistance, after 168 hours of aging according to the test parameters in Table 2, the physical property retention rate of the rubber stocks 2-4 is increased by not less than 5% compared with the rubber stock 1.

We claim:

1. A compound of Formula I:

(I)

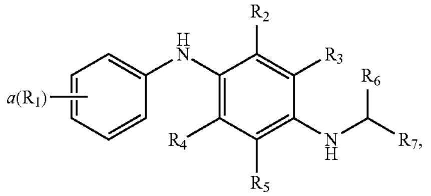

wherein each $R_1$ is independently a C1-C18 chain hydrocarbon group or a C3-C18 alicyclic hydrocarbon group, a is an integer of 1 to 5, at least one of the one or more $R_1$ is a methyl, and when a is 1, $R_1$ is at para-position to —NH group, and when a is 2 to 5, one of the $R_1$ is at the para-position to —NH group;

$R_2$, $R_3$, $R_4$, and $R_5$ are each independently H, a C1-C18 chain hydrocarbon group, or a C3-C18 alicyclic hydrocarbon group, and at least one of the $R_2$, $R_3$, $R_4$, and $R_5$ is not H; and $R_6$ and $R_7$ are each independently a C1-C18 chain hydrocarbon group or a C3-C18 alicyclic hydrocarbon group, or $R_6$ forms a C3-C18 aliphatic ring with $R_7$.

2. The compound according to claim 1, wherein each $R_1$ is independently a C1-C8 alkyl, a is 1 or 2;

$R_2$, $R_3$, $R_4$, and $R_5$ are each independently H or a C1-C8 alkyl, and two to three of $R_2$, $R_3$, $R_4$, and $R_5$ are H;

$R_6$ and $R_7$ are each independently a C1-C8 alkyl or a C3-C8 cycloalkyl, or $R_6$ forms a C3-C8 aliphatic ring with $R_7$.

3. A method for preparing the compound of claim 1, comprising:

(1) reacting a compound of Formula A and a compound of Formula B in a condensation reaction in presence of a first catalyst to obtain a condensate comprising a compound of Formula C, a compound of Formula C', or both, and reducing the condensate in presence of $H_2$ and a second catalyst to obtain a compound of Formula II:

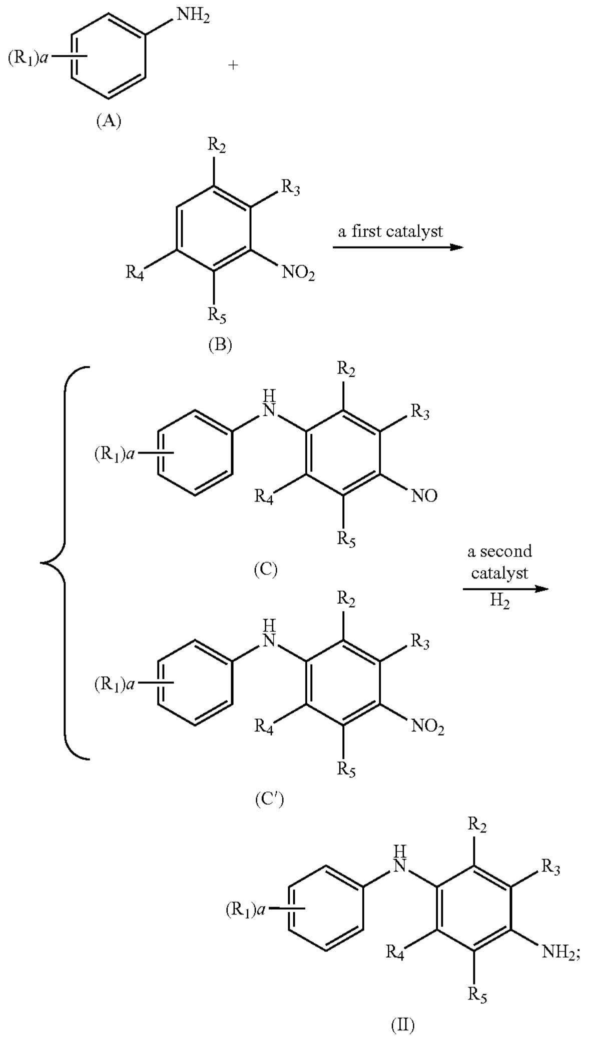

(A) (B) (C) (C') (II)

(2) reacting the compound of Formula II with a compound of Formula D in reductive alkylation in presence of $H_2$ and a third catalyst to obtain the compound of Formula I:

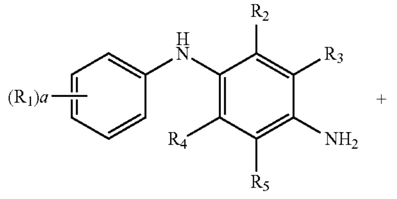

(II)

-continued

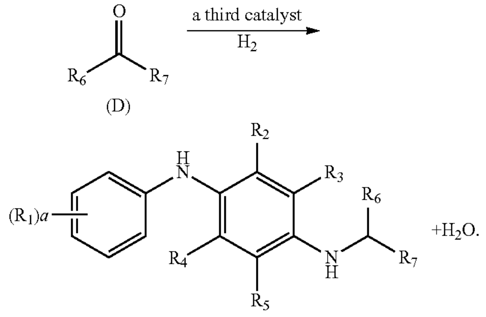

(D)

(I)

4. The method according to claim 3, wherein the first catalyst is an alkali metal hydroxide, an alkali metal alkoxide, a quaternary ammonium base, a combination of an alkali metal hydroxide and a halide of tetraalkyl ammonium, or a combination thereof.

5. The method according to claim 3, wherein the second catalyst is a porous metal catalyst or a supported metal catalyst.

6. The method according to claim 5, wherein the porous metal catalyst is Raney nickel, Raney cobalt, Raney copper, or a combination thereof.

7. The method according to claim 5, wherein the metal in the supported metal catalyst is nickel, cobalt, copper, platinum, palladium, ruthenium, rhodium, or a combination thereof, and the support in the supported metal catalyst is carbon, alumina, silica gel, molecular sieve, or a combination thereof.

8. The method according to claim 3, wherein the third catalyst is a supported metal catalyst.

9. The method according to claim 8, wherein the metal in the supported metal catalyst is nickel, cobalt, copper, platinum, palladium, ruthenium, rhodium, or a combination thereof, and the support in the supported metal catalyst is carbon, alumina, silica gel, molecular sieve, or a combination thereof.

10. The method according to claim 3, wherein in step (1), a molar ratio of the compound of Formula A to the compound of Formula B is 2:1 to 15:1.

11. The method according to claim 3, wherein in step (1), vacuum degree is −0.09 to −0.99 MPa.

12. The method according to claim 3, wherein in step (2), a molar ratio of the compound of Formula D to the compound of Formula II is 1:1 to 15:1.

13. A rubber composition, comprising the compound of claim 1.

14. A rubber product, comprising the rubber composition of claim 13.

15. The rubber product according to claim 14, wherein the rubber product is a tire.

16. A method for improving thermal oxidative aging resistance and/or UV aging resistance of rubber or a rubber product according to claim 1, comprising adding the compound of claim 1 to the rubber or rubber product.

17. The compound according to claim 1, wherein $R_2$, $R_3$, $R_4$, and $R_5$ are each independently H, a C1-C18 chain hydrocarbon group, or a C3-C18 alicyclic hydrocarbon group, one of the $R_2$, $R_3$, $R_4$, and $R_5$ is H, and other three groups of the $R_2$, $R_3$, $R_4$, and $R_5$ are not H.

* * * * *